United States Patent

Dingerdissen et al.

Patent Number: 6,143,934
Date of Patent: Nov. 7, 2000

[54] PREPARATION OF AMINES FROM OLEFINS OVER BORON BETA-ZEOLITES

[75] Inventors: Uwe Dingerdissen, Seeheim-Jugenheim; Rudolf Kummer, Frankenthal; Peter Stops, Altrip; Ulrich Müller, Neustadt; Jürgen Herrmann, Mannheim; Karsten Eller, Ludwigshafen, all of Germany

[73] Assignee: BASF Aktiengesellschaft, Ludwigshafen, Germany

[21] Appl. No.: 09/000,341

[22] PCT Filed: Aug. 19, 1996

[86] PCT No.: PCT/EP96/03634

§ 371 Date: Jan. 20, 1998

§ 102(e) Date: Jan. 20, 1998

[87] PCT Pub. No.: WO97/07088

PCT Pub. Date: Feb. 27, 1997

[30] Foreign Application Priority Data

Aug. 17, 1995 [DE] Germany .................. 195 30 177

[51] Int. Cl.[7] .................................................. C07C 209/00
[52] U.S. Cl. .................... 564/485; 564/395; 564/408; 564/445
[58] Field of Search .................. 564/485, 395, 564/408, 444.5

[56] References Cited

FOREIGN PATENT DOCUMENTS 2092964  6/1994  Canada .

OTHER PUBLICATIONS

Chemical Abstract 1987:600919, Hoelderich et al; abstract of de3634247, Jul. 1987.

Primary Examiner—Samuel Barts
Attorney, Agent, or Firm—Keil & Weinkauf

[57] ABSTRACT

In a process for preparing amines of the general formula I

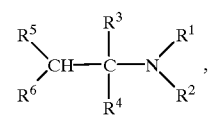

(I)

where
$R^1$, $R^2$, $R^3$, $R^4$, $R^5$, $R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ are together a saturated or unsaturated, divalent $C_3$–$C_9$-alkylene chain and $R^3$ and $R^5$ are each $C_{21}$–$C_{200}$-alkyl, $C_{21}$–$C_{200}$-alkenyl or together are a divalent $C_2$–$C_{12}$-alkylene chain, by reacting olefins of the general formula II

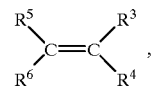

(II)

where $R^3$, $R^4$, $R^5$ and $R^6$ are as defined above, with ammonia or primary or secondary amines of the general formula III

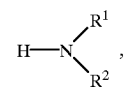

(III)

where $R^1$ and $R^2$ are as defined above, at from 200 to 350° C. and pressures of from 100 to 300 bar in the presence of a zeolitic catalyst, the zeolitic catalyst used is a boron BETA-zeolite.

12 Claims, No Drawings

PREPARATION OF AMINES FROM OLEFINS OVER BORON BETA-ZEOLITES

This application is a 371 of PCT/EP96/03634 filed Aug. 19, 1996.

The present invention relates to a process for preparing amines by reacting ammonia or primary or secondary amines with olefins at elevated temperatures and pressures in the presence of boron BETA-zeolites.

CA-A-2 092 964 discloses a process for preparing amines from olefins in which aluminum BETA-zeolites, which are defined as crystalline aluminosilicates of a definite composition and having a pore size of more than 5 Å, are used.

These catalysts leave something to be desired in terms of yield or space-time yield or rapid deactivation.

It is an object of the present invention to provide a solution to the above disadvantages.

We have found that this object is achieved by a novel and improved process for preparing amines of the general formula I

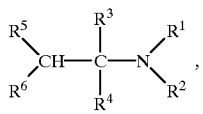

where
$R^1$, $R^2$, $R^3$, $R^4$, $R^5$, $R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl,
$R_1$ and $R^2$ are together a saturated or unsaturated, divalent $C_3$–$C_9$-alkylene chain and
$R^3$ and $R^5$ are each $C_{21}$–$C_{200}$-alkyl, $C_{21}$–$C_{200}$-alkenyl or together are a divalent $C_2$–$C_{12}$-alkylene chain,
by reacting olefins of the general formula II

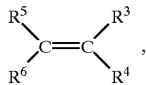

where $R^3$, $R^4$, $R^5$ and $R^6$ are as defined above, with ammonia or primary or secondary amines of the general formula III

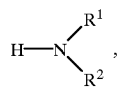

where $R^1$ and $R^2$ are as defined above, at from 200 to 350° C. and pressures of from 100 to 300 bar in the presence of a zeolitic catalyst, wherein the zeolitic catalyst used is a boron BETA-zeolite.

The process of the present invention can be carried out as follows:

The olefin II and ammonia or the primary or secondary amine III can be reacted at from 200 to 350° C., preferably from 220 to 330° C., particularly preferably from 230 to 320° C., and pressures of from 100 to 300 bar, preferably from 120 to 300 bar, particularly preferably from 140 to 290 bar, in the presence of a boron BETA-zeolite as catalyst, for example in a pressure reactor, and the amine obtained is preferably separated off and the unreacted starting materials are recirculated.

The present invention gives a very good yield at high selectivity and at high space-time yield. In addition, the deactivation of the catalyst has been suppressed.

The boron BETA-zeolites have, especially for this type of reaction (direct amination of olefins), a particularly favorable arrangement of the acid centers in combination with the characteristic size of the micropore system. This gives a high activity and a high operating life. The deactivation of the catalysts which is frequently found when using aluminum zeolites is attributed to the high acidity of the aluminum zeolites. For the same number of acid centers, boron zeolites have a significantly lower acid strength. The use of boron BETA-zeolite thus allows the advantages of the BETA-zeolite pore structure to be linked with the desired acidity.

Even with a low excess of ammonia or amine, the process of the present invention achieves a high selectivity of desired reaction product and dimerization and/or oligomerization of the olefin used is avoided.

One embodiment of the process comprises feeding ammonia and/or amines III mixed with the olefin II in a molar ratio of from 1:1 to 5:1 into a fixed-bed reactor and reacting the starting materials in the gas phase or in a supercritical state at a pressure of from 100 to 300 bar and at from 200 to 350° C.

The desired product can be obtained from the reactor output by means of known methods, for example distillation or extraction, and if necessary brought to the desired purity by means of further separation operations. Preference is generally given to recirculating the unreacted starting materials to the reactor.

It is possible to use monounsaturated or polyunsaturated olefins II, in particular those having from 2 to 10 carbon atoms, or their mixtures or polyolefins as starting materials. Owing to their less pronounced tendency to polymerize, monoolefins are better suited than diolefins and polyolefins, although these can be reacted as selectively with the aid of higher excesses of ammonia or amine. The position of the equilibrium and thus the conversion to the desired amine is very strongly dependent on the reaction pressure selected. High pressure favors the addition product, but for technical and economic reasons, the pressure range up to 300 bar generally represents the optimum. The selectivity of the reaction is influenced not only by parameters such as ammonia/amine excess and catalyst, but to a great degree by the temperature. Although the reaction rate of the addition reaction increases strongly with rising temperature, competing cracking and recombination reactions of the olefin are promoted at the same time. In addition, a temperature increase is not advantageous from a thermodynamic point of view. The position of the temperature optimum with regard to conversion and selectivity is dependent on the constitution of the olefin, the amine used and the catalyst and is usually in the range from 200 to 350° C.

Suitable catalysts for the amination of olefins are boron BETA-zeolites which can be prepared, for example, as described in Gaodeng Xuexiao Huaxue Xuebao (1993), 14(2), 159–163 or Gaodeng Xuexiao Huaxue Xuebao (1989), 10(7), 677–682 or WO-A-92/20446.

The boron BETA-zeolites, which are preferably used in the H form, can be shaped into extrudates or pellets as such or using a binder in a weight ratio of from 98:2 to 40:60. Suitable binders are the various aluminum oxides, preferably boehmite, amorphous aluminosilicates having an $SiO_2$/$Al_2O_3$ ratio of from 25:75 to 95:5, silicon dioxide, preferably finely divided SiO$_2$, mixtures of finely divided SiO$_2$ and finely divided Al$_2$O$_3$, finely divided TiO$_2$ and also clays. After the shaping process, the extrudates or compacts are advantageously dried for 16 hours at 110° C. and calcined for from 2 to 16 hours at from 200 to 500° C.; the calcination can also be carried out directly in the amination reactor.

To increase the selectivity, the operating life and the number of possible regenerations, various modifications can be carried out on zeolitic catalysts.

One modification of the catalysts comprises ion-exchanging or doping the unshaped or shaped zeolites with alkali metals such as Na and K, alkaline earth metals such as Ca, Mg, earth metals such as Tl, transition metals such as Mn, Fe, Mo, Cu, Zn, Cr, noble metals and/or rare earth metals such as La, Ce or Y.

An advantageous embodiment comprises placing the shaped boron BETA-zeolites in a flow tube and passing, for example, a halide, acetate, oxalate, citrate or nitrate of the above-described metals in dissolved form over them at from 20 to 100° C. Such an ion exchange can be carried out, for example, on the hydrogen, ammonium or alkali metal form of the zeolites.

Another possible way of applying the metals to the zeolites comprises impregnating the zeolitic material with, for example, a halide, acetate, oxalate, citrate, nitrate or oxide of the above-described metals in aqueous or alcoholic solution.

Either ion exchange or impregnation can be followed by drying, if desired repeated calcination. In the case of metal-doped zeolites, post-treatment with hydrogen and/or water vapor can be useful.

A further possible way of effecting the modification comprises subjecting the zeolitic material, shaped or unshaped, to treatment with acids such as hydrochloric acid (HCl), hydrofluoric acid (HF), oxalic acid (H$_2$C$_2$O$_4$), sulfuric acid (H$_2$SO$_4$), phosphoric acid (H$_3$PO$_4$) or mixtures thereof.

A particular embodiment comprises treating the zeolitic powder before it is shaped with a 0.001–2 N solution, preferably a 0.05–0.5 N solution, of one of the specified acids for from 1 to 100 hours under reflux. After filtering off and washing, the powder is generally dried at from 100 to 160° C. and calcined at from 200 to 600° C. A further particular embodiment comprises acid treatment of the zeolites after they have been shaped using binder. In this embodiment, the zeolite is generally treated with a 3–25% strength, in particular with a 12–20% strength, acid for from 1 to 3 hours at from 60 to 80° C., subsequently washed, dried at from 100 to 160° C. and calcined at from 200 to 600° C.

Another possible way of effecting the modification is provided by exchange with ammonium salts, eg. with NH$_4$Cl or with monoamines, diamines or polyamines. In this procedure, the zeolite shaped using binder is generally continuously exchanged at from 60 to 80° C. for 2 hours using a 10–25% strength, preferably 20% strength, NH$_4$Cl solution in a weight ratio of zeolite/ammonium chloride solution of 1:15 and is then dried at from 100 to 120° C.

A further modification which can be made to the boron BETA-zeolites is deboration, in which part of the boron atoms is replaced by silicon or the boron content of the zeolites can be reduced by, for example, by hydrothermal treatment. A hydrothermal deboration is advantageously followed by an extraction with acids or complexing agents in order to remove non-lattice boron formed. The replacement of boron by silicon can be carried out, for example, by means of (NH$_4$)$_2$SiF$_6$ or SiCl$_4$.

The replacement of boron by silicon in boron BETA-zeolites using SiCl$_4$ is known from U.S. Pat. No. 4,701,313.

The catalysts can be used for the amination of the olefins as extrudates having a diameter of, for example, from 1 to 4 mm or as pellets having a diameter of, for example, from 3 to 5 mm.

The catalyst, for example shaped into extrudates, can be converted by milling and sieving into a fluidizable material having a particle size of from 0.1 to 0.8 mm.

The substituents $R^1$, $R^2$, $R^3$, $R^4$, $R^5$ and $R^6$ in the compounds I, II and III have the following meanings:

$R^1$, $R^2$, $R^3$, $R^4$, $R^5$, $R^6$ hydrogen,

C$_1$–C$_{20}$-alkyl, preferably C$_1$–C$_{12}$-alkyl, particularly preferably C$_1$–C$_8$-alkyl such as methyl, ethyl, n-propyl, iso-propyl, n-butyl, iso-butyl, sec-butyl, tert-butyl, n-pentyl, iso-pentyl, n-hexyl, iso-hexyl, n-heptyl, iso-heptyl, n-octyl and iso-octyl, C$_2$–C$_{20}$-alkenyl, preferably C$_2$–C$_{12}$-alkenyl, particularly preferably C$_2$–C$_8$-alkenyl such as vinyl and allyl, C$_2$–C$_{20}$-alkynyl, preferably C$_2$–C$_{12}$-alkynyl, particularly preferably C$_2$–C$_8$-alkynyl such as C$_2$H and propargyl, C$_3$–C$_{20}$-cycloalkyl, preferably C$_3$–C$_{12}$-cycloalkyl, particularly preferably C$_5$–C$_8$-cycloalkyl such as cyclopentyl, cyclohexyl, cycloheptyl and cyclooctyl, C$_4$–C$_{20}$-alkylcycloalkyl, preferably C$_4$–C$_{12}$-alkylcycloalkyl, particularly preferably C$_5$–C$_{10}$-alkylcycloalkyl such as 2-methylcyclopentyl and 4-methylcyclohexyl, C$_4$–C$_{20}$-cycloalkylalkyl, preferably C$_4$–C$_{12}$-cycloalkylalkyl, particularly preferably C$_5$–C$_{10}$-cycloalkylalkyl such as cyclopentylmethyl and cyclohexylmethyl, aryl such as phenyl, 1-naphthyl and 2-naphthyl, preferably phenyl, C$_7$–C$_{20}$-alkylaryl, preferably C$_7$–C$_{16}$-alkylaryl, particularly preferably C$_7$–C$_{12}$-alkylphenyl such as 2-methylphenyl, 3-methylphenyl, 4-methylphenyl, 2-ethylphenyl, 3-ethylphenyl and 4-ethylphenyl, C$_7$–C$_{20}$-aralkyl, preferably C$_7$–C$_{16}$-aralkyl, particularly preferably C$_7$–C$_{12}$-phenalkyl such as phenylmethyl, 1-phenylethyl and 2-phenylethyl, $R^1$ and $R^2$ together a saturated or unsaturated, divalent C$_3$–C$_9$-alkylene chain, preferably —(CH$_2$)$_4$—, —(CH$_2$)$_5$—, —(CH$_2$)$_7$— and —CH=CH—C=CH—, $R^3$ or $R^5$ C$_{21}$–C$_{200}$-alkyl, preferably C$_{40}$–C$_{200}$-alkyl such as polybutyl, polyisobutyl, polypropyl, polyisopropyl and polyethyl, particularly preferably polybutyl and polyisobutyl, C$_{21}$–C$_{200}$-alkenyl, preferably C$_{40}$–C$_{200}$-alkenyl, particularly preferably C$_{70}$–C$_{170}$-alkenyl, $R^3$ and $R^5$ together a divalent C$_2$–C$_{12}$-alkylene chain, preferably a divalent C$_3$–C$_8$-alkylene chain, particularly preferably —(CH$_2$)$_3$—, —(CH$_2$)$_4$—, —(CH$_2$)$_5$—, —(CH$_2$)$_6$— and —(CH$_2$)$_7$—, in particular —(CH$_2$)$_3$— and —(CH$_2$)$_4$—.

EXAMPLES

Catalyst Synthesis 60 g of boric acid (H$_3$BO$_3$) were dissolved in a solution comprising 206 g of distilled water and 344 g of 40% strength tetraethyl-ammonium hydroxide solution and transferred to an autoclave. After addition of 550 g of Ludox® AS 40 (42% SiO$_2$, Du Pont), the autoclave was closed and the mixture was crystallized for 216 hours at 150° C. The boron BETA-zeolite formed was filtered off, washed with distilled water until neutral, dried for 24 hours at 120° C. and calcined for 5 hours at 500° C.

Examples of Catalyst Extrusion

Catalyst A 100 g of boron BETA-zeolite ($SiO_2/B_2O_3=20$) were admixed with 23.8 g of Ludox® (42% $SiO_2$, Du Pont) and 5 g of starch. The mixture was compacted in a kneader and kneaded with careful addition of water (64 ml). The kneading time was 60 minutes. In a ram extruder, 2 mm extrudates were produced using a pressing pressure of 90 bar. The extrudates were dried for 60 hours at 110° C. and subsequently calcined for 16 hours at 500° C.

Catalyst B 60 g of boron BETA-zeolite ($SiO_2/B_2O_3=20$) were admixed with 40 g of boehmite and 2 g of formic acid. The mixture was compacted in a kneader and kneaded with careful addition of water (57 ml). The kneading time was 60 minutes. In a ram extruder, 2 mm extrudates were produced using a pressing pressure of 100 bar. The extrudates were dried for 16 hours at 110° C. and subsequently calcined for 16 hours at 500° C.

Catalyst C

Catalyst C was prepared using a method similar to catalyst A, but using a boron BETA-zeolite having an $SiO_2/B_2O_3$ ratio of 19.

Catalyst D

Catalyst D was prepared using a method similar to catalyst B, but using a boron BETA-zeolite having an $SiO_2/B_2O_3$ ratio of 19.

Catalyst H

Catalyst H was prepared using a method similar to catalyst B, but using a boron BETA-zeolite having an $SiO_2/B_2O_3$ ratio of 23.

Amination examples

A 0.3 l stirring autoclave was charged with 10 g of one of the catalysts described above and, after being closed, was pressurized with the olefin and ammonia or amine. The amount of starting material was either such that at the selected reaction temperature, the desired pressure was reached as intrinsic pressure of the reactants or nitrogen was additionally injected. The molar ratio of ammonia/amine to olefin was varied from 1:1 to 5:1, the reaction time was fixed at 16 hours.

The liquid and gas phases of the reaction product were separately analyzed by gas chromatography. The conversions shown in the tables are always based on the olefin; the selectivities shown are based on the main products: cyclohexylamine from cyclohexene, cyclopentylamine from cyclopentene, tert-butylamine from isobutene.

As an alternative, the experiments were carried out in a tube reactor (6 mm internal diameter) under isothermal conditions at from 260 to 300° C. and at a pressure of 280 bar using a mixture of isobutene and ammonia in a molar ratio of 1:1.5. The reaction products were analyzed by gas chromatography.

The results using the various catalysts are shown in Tables 1 to 3.

TABLE 1 tert-Butylamine ($NH_3$: $C_4H_8$ = 1.5)

| | Proportion of extrusion aid | | Pressure | Temp. | tert-Butyl yield [% by weight] | | | | Density |
|---|---|---|---|---|---|---|---|---|---|
| Catalyst | $Al_2O_3$ [%] | $SiO_2$ [%] | [bar] | [° C.] | WHSV 0.5 g/g.h | WHSV 0.7 g/g.h | WHSV 1.5 g/g.h | WHSV 3 g/g.h | [kg/l] |
| A | | 9 | 280 | 270 | | 22.67 | 21.44 | 18.33 | 0.50 |
| B | 40 | | 280 | 260 | | 22.95 | | | 0.61 |
| B | 40 | | 280 | 270 | | 21.66 | 20.52 | 17.71 | 0.61 |
| B | 40 | | 280 | 280 | | | 18.12 | 16.83 | 0.61 |
| B | 40 | | 280 | 300 | | | | 12.80 | 0.61 |
| A | | 9 | 280 | 280 | | 18.83 | 18.78 | 17.98 | 0.50 |
| A | | 9 | 280 | 300 | | | | 12.28 | 0.50 |
| A | | 9 | 280 | 260 | 25.86 | 24.04 | 20.35 | 16.34 | 0.50 |
| C | | 9 | 280 | 270 | | 21.63 | 21.27 | 20.87 | 0.45 |
| D | 40 | | 280 | 270 | | 22.80 | 20.34 | 18.21 | 0.52 |
| E | 20 | | 280 | 270 | | 22.00 | 20.95 | 18.20 | 0.43 |
| F | 40 | | 280 | 270 | | 22.24 | 21.08 | 18.78 | 0.54 |
| G | | 9 | 280 | 270 | | 21.30 | 20.45 | 18.55 | 0.48 |
| H | 40 | | 280 | 270 | | 20.93 | 20.51 | 18.44 | 0.57 |

Catalyst E

Catalyst E was prepared using a method similar to catalyst D, but using only 20 g of boehmite.

Catalyst F

Catalyst F was prepared using a method similar to catalyst B, but using a boron BETA-zeolite having an $SiO_2/B_2O_3$ ratio of 19.

Catalyst G

Catalyst G was prepared using a method similar to catalyst A, but using a boron BETA-zeolite having an $SiO_2/B_2O_3$ ratio of 23.

TABLE 2

Cyclopentylamine ($NH_3$: $C_5H_8$ = 3)

| Catalyst | Pressure [bar] | Temperature [° C.] | Cyclohexylamine [mol %] |
|---|---|---|---|
| B-BETA, $SiO_2/B_2O_3$ = 20 | 425 | 300 | 7.6 |

TABLE 3

Cyclohexylamine (NH$_3$: C$_6$H$_{10}$ = 3)

| Catalyst | Pressure [bar] | Temperature [° C.] | Cyclohexylamine [mol %] |
|---|---|---|---|
| B-BETA, SiO$_2$/B$_2$O$_3$ = 20 | 380 | 300 | 7.1 |

In addition, the catalyst F was also tested for operating life in a continuous experiment. 50 g of catalyst F were installed in a tube reactor (15 mm internal diameter) provided with built-in thermocouple sheath for measuring the internal temperature. Steatite as inert material was placed in the tube reactor both above and below the catalyst bed (72 cm height). The heating of the reactor and the preheating of the feed mixture were each carried out by means of oil baths, the feed to the reactor was from the top and the product mixture was depressurized in two stages (280 bar→20 bar→1 bar). Operation at 275° C. and 280 bar, a WHSV of 3 g/g·h and an NH$_3$:isobutene ratio of 1.5:1 for a period of 1100 hours gave a constant TBA yield of 17.3% by weight, without any incipient deactivation being observed.

We claim:

1. A process for preparing amines of the formula I

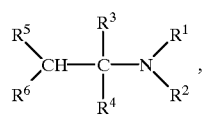
(I)

where

R$^1$, R$^2$, R$^3$, R$^4$, R$^5$, R$^6$ are hydrogen, C$_1$–C$_{20}$-alkyl, C$_2$–C$_{20}$-alkenyl, C$_2$–C$_{20}$-alkynyl, C$_3$–C$_{20}$-cycloalkyl, C$_4$–C$_{20}$-alkylcycloalkyl, C$_4$–C$_{20}$-cycloalkylalkyl, aryl, C$_7$–C$_{20}$-alkylaryl or C$_7$–C$_{20}$-aralkyl, R$^1$ and R$^2$ are together a saturated or unsaturated, divalent C$_3$–C$_9$-alkylene chain, and R$^3$ and R$^5$ are each C$_{21}$–C$_{200}$-alkyl, C$_{21}$–C$_{200}$-alkenyl or together are a divalent C$_2$–C$_{12}$-alkylene chain, by reacting olefins of the formula II

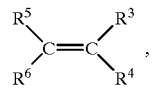
(II)

with ammonia or primary or secondary amines of the formula III

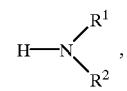
(III)

at from 200 to 350° C. and pressures of from 100 to 300 bar in the presence of a zeolitic catalyst, wherein the zeolitic catalyst is a boron BETA-zeolite.

2. The process defined in claim 1, wherein the boron BETA-zeolite is in the H form.

3. The process defined in claim 1, wherein the amine I is separated off and the unreacted starting materials II and III are recirculated.

4. The process defined in claim 1, wherein the olefin II is isobutene, diisobutene, cyclopentene, cyclohexene or polyisobutene.

5. The process defined in claim 1, wherein the boron BETA-zeolite is pre-treated with an acid.

6. The process defined in claim 1, wherein the boron BETA-zeolite is doped with one or more transition metals.

7. The process defined in claim 1, wherein the boron BETA-zeolite is doped with one or more elements of the rare earths.

8. The process defined in claim 1, wherein the boron BETA-zeolite is doped with one or more elements selected from the group consisting of the alkali metals, alkaline earth metals and earth metals.

9. The process defined in claim 1, wherein the boron BETA-zeolite is in the ammonium form.

10. The process defined in claim 1, wherein the boron BETA-zeolite is shaped using a binder and calcined at from 200 to 600° C.

11. The process defined in claim 1, wherein the boron BETA-zeolite has a boron content which is reduced after synthesis.

12. The process defined in claim 5, wherein the boron BETA-zeolite is pre-treated with an acid selected from the group consisting of hydrochloric acid, hydrofluoric acid, sulfuric acid, oxalic acid and phosphoric acid.

* * * * *